US009349067B2

(12) United States Patent
Kelly

(10) Patent No.: US 9,349,067 B2
(45) Date of Patent: May 24, 2016

(54) METHOD AND APPARATUS FOR CORRECTING MEDICAL IMAGING DATA

(71) Applicant: Matthew David Kelly, Botley (GB)

(72) Inventor: Matthew David Kelly, Botley (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 397 days.

(21) Appl. No.: 13/650,337

(22) Filed: Oct. 12, 2012

(65) Prior Publication Data

US 2013/0094727 A1 Apr. 18, 2013

(30) Foreign Application Priority Data

Oct. 14, 2011 (GB) .................................. 1117808.4

(51) Int. Cl.
*G06K 9/00* (2006.01)
*G06K 9/40* (2006.01)
*G06T 7/00* (2006.01)
*A61B 6/03* (2006.01)
*A61B 6/00* (2006.01)

(52) U.S. Cl.
CPC ............... *G06K 9/40* (2013.01); *A61B 6/5217* (2013.01); *G06T 7/0081* (2013.01); *A61B 6/037* (2013.01); *A61B 6/461* (2013.01); *A61B 6/467* (2013.01); *A61B 6/5229* (2013.01); *G06T 2207/10104* (2013.01); *G06T 2207/20012* (2013.01); *G06T 2207/20104* (2013.01); *G06T 2207/30004* (2013.01)

(58) Field of Classification Search
CPC ................ A61B 6/5217; G01T 1/1663; G06T 220/10104; G06T 2207/20012
See application file for complete search history.

(56) References Cited

U.S. PATENT DOCUMENTS

| 7,817,831 | B2 * | 10/2010 | Scheuering | G06T 7/0081 382/128 |
| 8,670,602 | B2 * | 3/2014 | Schmainda | A61B 5/0263 382/128 |
| 2002/0172323 | A1 * | 11/2002 | Karellas | G01F 1/66 378/51 |
| 2005/0129170 | A1 * | 6/2005 | Watson | G01T 7/005 378/5 |
| 2006/0034765 | A1 * | 2/2006 | Schmainda | A61K 49/06 424/9.3 |

(Continued)

FOREIGN PATENT DOCUMENTS

| GB | 2464210 A | 4/2010 | |
| GB | 2495603 A * | 4/2013 | ............... G06K 9/40 |

(Continued)

OTHER PUBLICATIONS

N. Long et al., "Causes and imaging features of false positives and false negatives on 18F-PET/CT in oncologic imaging", 2011, Insights Imaging, p. 679-698.*

Dandekar, M. et al., "Reproducibility of 18F-FDG microPET Studies in Mouse Tumor Xenografts", Apr. 2007, Journal of Nuclear Medicine, p. 1-14.*

"Quantitative analysis of PET studies," Weber, Radiotherapy and Oncology (2010), pp. 308-310.

(Continued)

*Primary Examiner* — Gandhi Thirugnanam
(74) *Attorney, Agent, or Firm* — Schiff Hardin LLP

(57) ABSTRACT

In a method and apparatus for correcting image data from a medical imaging scan of a subject, into which subject a specified amount of an imaging substance has been introduced, a region of the image data, containing an anomalous proportion of the imaging substance introduced, is identified. For the identified region a regional value of a variable in the image data associated with the imaging substance is determined. The regional value is used to determine the proportion of the substance in the region, and the proportion is subtracted from the specified amount of the imaging substance.

11 Claims, 2 Drawing Sheets

(56) References Cited

U.S. PATENT DOCUMENTS

| | | | | |
|---|---|---|---|---|
| 2007/0043286 | A1* | 2/2007 | Lu | A61N 5/103 600/407 |
| 2007/0066892 | A1* | 3/2007 | Haras | A61B 6/032 600/425 |
| 2008/0013672 | A1* | 1/2008 | Krauss | A61B 6/482 378/4 |
| 2011/0207828 | A1* | 8/2011 | Miller | A61K 31/122 514/678 |
| 2012/0308106 | A1* | 12/2012 | Kelly | G06T 7/20 382/131 |
| 2013/0131422 | A1* | 5/2013 | Vosniak | A61B 6/037 600/1 |

FOREIGN PATENT DOCUMENTS

| | | |
|---|---|---|
| WO | 2011010231 A1 | 1/2011 |
| WO | 2011070484 A2 | 6/2011 |

OTHER PUBLICATIONS

"Is there a necessity of Standard Uptake Value correction in liver reference level?" (Abstract) The Institution of Engineering and Technology, World Congress on Medical Physics and Biomedical Engineering (2009).

* cited by examiner

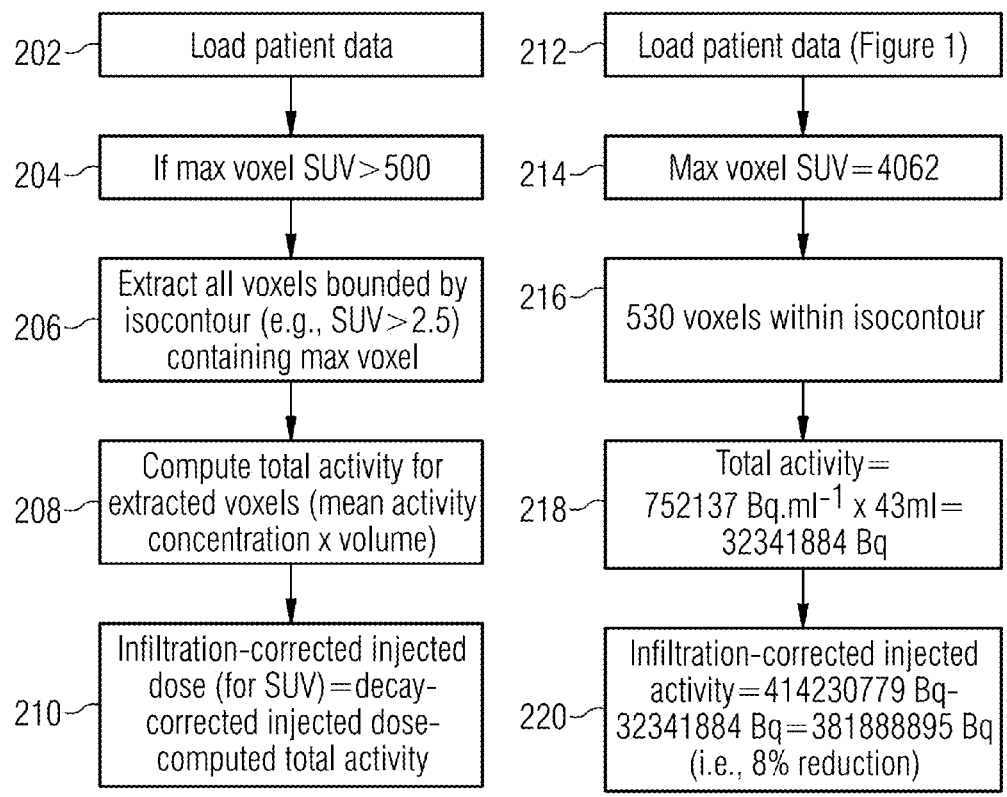
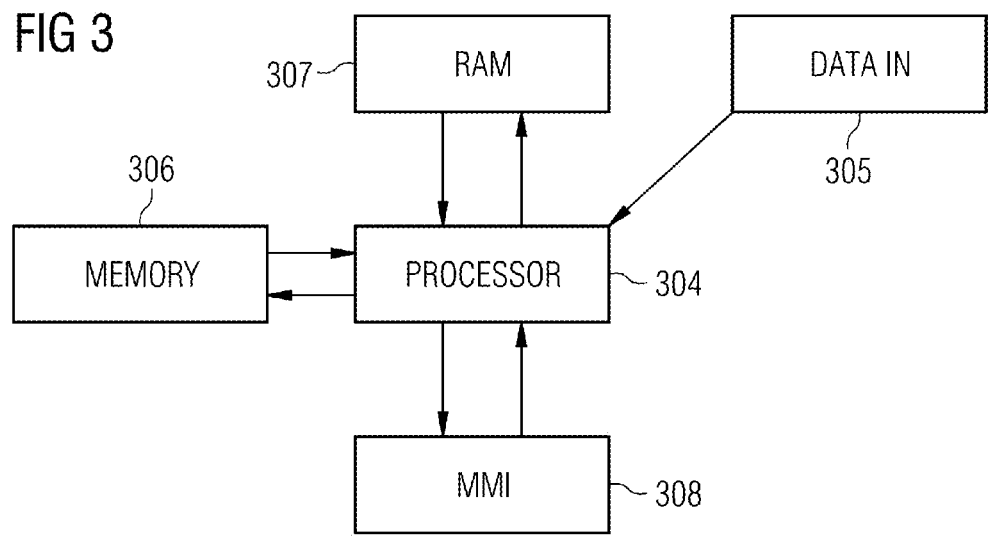

METHOD AND APPARATUS FOR CORRECTING MEDICAL IMAGING DATA

BACKGROUND OF THE INVENTION

1. Field of the Invention

This invention is directed to methods and apparatus for correcting for image data from a medical imaging scan of a subject, into which subject a specified amount of an imaging substance has been introduced, in particular to dose infiltration in PET imaging.

2. Description of the Prior Art

In the medical imaging field, several imaging schemes are known. For example PET (Positron Emission Tomography) is a method for imaging a subject in 3D using an injected radioactive substance which is processed in the body, typically resulting in an image indicating one or more biological functions. Other such functional imaging modalities are known, such as SPECT.

In such functional images, many important pathologies and anatomical structures appear as very high (or low) intensities. For example, a tumour in an FDG-PET image will often appear as a bright region.

When a PET radiotracer is injected into a patient, dose infiltration may occur when not all of the radiotracer is injected into the vein. The maximal intensity projection (100) shown in FIG. 1 illustrates a case with dose infiltration at the injection site (102). The infiltration can be seen as highly increased uptake in the region (104) around the injection site. In this case the maximum SUV at the site of infiltration is more than 4000.

The potential impacts of this on the clinical workflow are as follows:

1. Axial slices in which an infiltration site is present suffer from reduced intensity granularity due to rescale slope and intercept (RSI) encoding in DICOM, in addition to other image artifacts that affect the clinical readability of those slices.

2. Standardized Uptake Values (SUVs) for the entire patient are no longer reliable as the infiltrated dose is not able to circulate around the body, so only a fraction of the injected dose is available for uptake by tissue.

Regarding the first of the potential clinical impacts listed above, if the dose infiltration is detected before the patient leaves imaging facility, the bed position affected by the infiltration site can be rescanned with the infiltration site moved outside the field of view (FOV).

Rescanning the affected bed position will not, however, address the second problem of unreliable SUVs. This can only be addressed by repeating the entire imaging process at a later time, exposing the patient to additional dose from the radiotracer and the CT scan for attenuation correction.

Dose infiltration also affects other imaging modalities (such as MR, or ultrasound) in which imaging substances are introduced to the subject, where not all of the imaging substance is properly introduced, either by injection or insertion, so that the initial amount of the imaging substance is reduced by an unknown proportion.

SUMMARY OF THE INVENTION

An object of the present invention is to address the above-described problems and to provide improvements upon the known devices and methods.

In general terms, an embodiment of a method according to the invention for correcting image data supplied to a computerized processor from a medical imaging scan of a subject, into which subject a specified amount of an imaging substance has been introduced, includes, in the processor, identifying a region of the image data containing an anomalous proportion of the imaging substance introduced, determining for the identified region a regional value of a variable in the image data associated with the imaging substance, using the regional value to determine the proportion of the substance in the region, subtracting the proportion from the specified amount of the imaging substance to obtain a corrected amount of the imaging substance, and making an indication of the corrected amount available from the processor.

This allows a simple of correction of the amount of the imaging substance which is used for later calculation, by the amount lost by anomalous introduction into the subject, for example by dose infiltration into tissue surrounding a vein.

Preferably, the imaging substance is a pharmaceutical tracer. More preferably, the variable is activity of the tracer. Still more preferably, the step of determining comprises measuring an SUV value for the region.

The method can further include determining the mean activity concentration in the identified region, and a volume, to determine a total activity in the identified region.

Preferably, the steps of using and subtracting include subtracting the total activity from a decay-corrected dose introduced.

In an embodiment, the identified region is an infiltration site of the subject.

Suitably, the anomalous proportion is a part of a dose not injected into a vein.

In one embodiment, the step of identifying is registering (entering) a user selection of the region.

In another embodiment, the step of identifying is detecting a region in the image data having activity over a given threshold.

Preferably, the region detected includes one or more voxels having a value of SUV over the threshold.

More preferably, the method further includes segmenting the detected region, for example using an isocontour at a predetermined percentage of a maximum activity value for the region.

In one embodiment, the method further includes initially comparing the image data to an anatomical atlas, and identifying, as candidates for selection, regions of the image data corresponding to regions in the atlas marked as possible sites of anomalous introduction of the substance.

The invention also encompasses an apparatus for correcting for image data from a medical imaging scan of a subject, into which subject a specified amount of an imaging substance has been introduced. The apparatus includes a processor configured to identify a region of the image data containing an anomalous proportion of the imaging substance introduced, determine for the identified region a regional value of a variable in the image data associated with the imaging substance, use the regional value to determine the proportion of the substance in the region, and subtract the proportion from the specified amount of the imaging substance; and a monitoring device configured to indicate the corrected amount of the imaging substance to a user.

The present invention also encompasses a non-transitory, computer-readable data storage medium encoded with programming instructions that, when the storage medium is loaded into a computerized processor, cause the processor to implement one or more of the embodiments of the inventive method described above.

BRIEF DESCRIPTION OF THE DRAWINGS

FIG. 2 shows flowcharts illustrating steps according to embodiments of the invention.

FIG. 3 illustrates an apparatus according to an embodiment of the invention.

DESCRIPTION OF THE PREFERRED EMBODIMENTS

Figure 1:
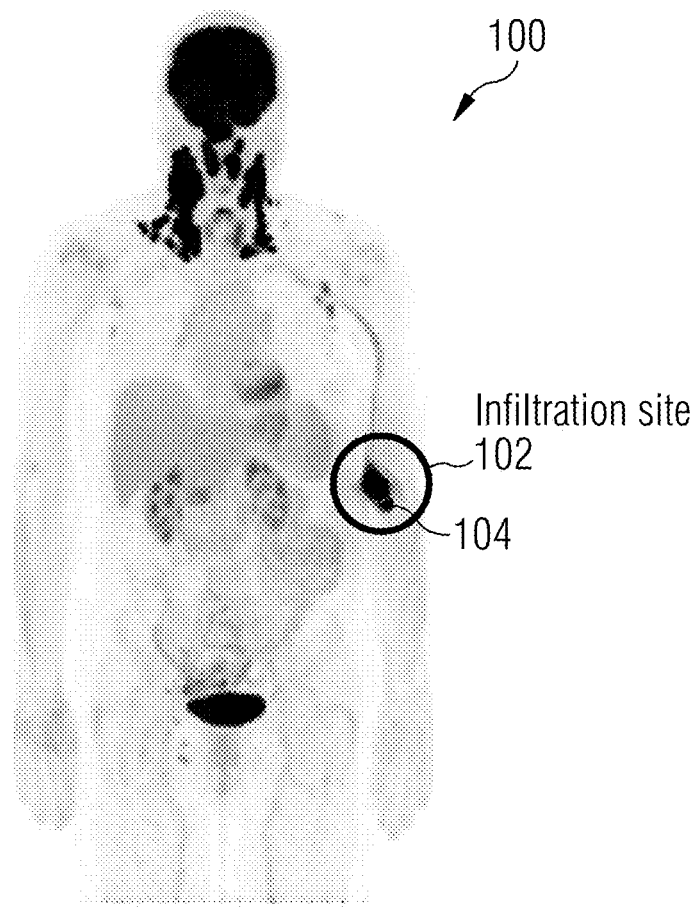
FIG. 1 illustrates a dose infiltration site in a MIP according to an embodiment of the invention.

When the following terms are used herein, the accompanying definitions are applicable:
PET—Positron Emission Tomography
SUV—Standardised Uptake Value
FDG—F-18 fluorodeoxyglucose, a PET radiotracer
MIP—Maximum Intensity Projection (or Minimum Intensity Projection, usually denoted MinIP)
MRI—Magnetic Resonance Imaging
ROI/VOI—Region/volume of interest.
CT—Computed Tomography
DICOM—Digital Imaging and Communications in Medicine
FOV—Field Of View
RSI—Rescale Slope and Intercept The invention provides a method for correcting for inadvertent introduction of some imaging substance at a site in the subject, by assessing the region containing the substance (inadvertently introduced) and comparing this with the initial amount of the substance introduced.

Embodiments of the invention provide features such as
automatically detecting non-circulating radiotracer (infiltration) at the injection site and correcting injected-dose-normalised measures of radiotracer uptake
the presence of dose infiltration is detected based upon the presence of abnormally-high activity concentration
the activity trapped at the infiltration site is classified and measured using an isocontour delineated sub-volume
the trapped activity measured is subtracted from the (decay-corrected) total injected activity for re-computation of correcting injected-dose-normalised measures of radiotracer uptake
detection of dose infiltration is refined using anatomical information, for example, registration to an anatomical atlas to restrict search to the arms.

An embodiment of the invention allows the system to provide corrected SUVs that account for non-circulating tracer trapped at an infiltration site. In this embodiment, it does this as follows, with reference to FIG. 2:

1. The patient data is loaded (202), and the user manually identifies and delineates the infiltration site in the image reviewing software. Alternatively, the infiltration site could be automatically identified by the system by detecting (204) any voxels with an SUV over a given threshold (e.g., 500) then segmenting (206) the surrounding region using an isocontour (e.g., at some fixed percentage of SUVmax).

2. The total activity (208) in the delineated infiltration site is calculated (i.e., mean activity concentration (Bq.ml-1)× volume (ml)).

3. The infiltration activity is then subtracted (210) from the decay-corrected injected dose value used in the computation of SUV:

$$SUV = \frac{C}{D-I} * W$$

where C is the activity concentration measured in a voxel or region of interest (Bq.ml-1), D is the dose injected (Bq) following decay correction to image start time, I is the measured infiltration activity (Bq), and W is the patient weight (g).

The second flow chart in FIG. 2 gives an example, which is based on the subject image data record captured and illustrated in FIG. 1. The loaded patient data (212) returns a maximum voxel SUV of 4062 (214), which not only indicates an anomaly at the site 102, but indicates the location of the site.

The isocontour segmented has 530 voxels surrounding the site (216), and total activity is then calculated and subtracted to find the corrected dose (218, 220).

When using the automated method for finding the infiltration site, it is notable that by the time (at the time point in the data set) the infiltration is clear in the image data, the tracer injected which has entered the vein correctly, will have long passed away from the injection site into the subject, and therefore any remaining activity in this region should be that due to the does infiltration. A correction for any background activity can be performed if necessary.

The automatic detection of the infiltration site can be refined using an anatomical atlas, e.g., by restricting the search to potential injection sites such as the arms.

If the infiltration activity is very high, the imaging system may underestimate the true counts measured (due to saturation/dead time etc.). In such cases, an additional correction for this may be applied where available.

The infiltration site could be detected at image acquisition (by an unusually high number of counts in the sinogram bins corresponding to a particular region. Auto correction could then be performed at this point by providing a corrected injected dose in the DICOM header for SUV computation (as described above). Furthermore, the activity stored in the reconstructed image voxels at the infiltration site could be reduced to a less extreme value so as to improve the granularity of intensity values in those image slices following RSI encoding.

In other embodiments of the invention, the assessment of the anomalous introduction of the imaging substance can be applied to other imaging modalities using imaging substances, such as MR, or ultrasound. For example, in the case of MR, the use of contrast agents can be affected by infiltration or leakage of the agent into unintended areas. In similar fashion to the above method, the region of the imaging data of the subject affected can be obtained, and the amount of agent in the region identified, and subtracted from the initial amount introduced. For example, the additional contrast in the region selected could be measured, either directly or in comparison with a background, and this compared to the contrast expected for a standard amount of the agent, and this used to calculate the amount of agent in the affected area.

Referring to FIG. 3, the above embodiments of the invention may be conveniently realized as a computer system suitably programmed with instructions for carrying out the steps of the methods according to the invention.

For example, a central processing unit 304 receives data representative of medical scans via a port 305 which could be a reader for portable data storage media (e.g. CD-ROM); a direct link with apparatus such as a medical scanner (not shown) or a connection to a network. For example, in an embodiment, the processor performs such steps as: identifying a region of the image data containing an anomalous proportion of the imaging substance introduced; determining for the identified region a regional value of a variable in the image data associated with the imaging substance; using the regional value to determine the proportion of the substance in the region; and subtracting the proportion from the specified amount of the imaging substance.

Software applications loaded on memory 306 are executed to process the image data in random access memory 307.

A Man—Machine interface 308 typically includes a keyboard/mouse/screen combination (which allows user input such as initiation of applications) and a screen on which the results of executing the applications are displayed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method of correcting for image data supplied to a computerized processor from a medical imaging scan of a subject, into which subject a specified amount of a pharmaceutical tracer has been introduced, comprising, in the processor, the steps of:
   accessing anatomical data in an anatomical atlas and comparing the image data to said anatomical data, and identifying a set of candidate regions of the image data that correspond respectively to regions in the anatomical atlas marked as likely sites of introduction of the pharmaceutical tracer into the subject;
   detecting a region of the image data that represents activity produced by said pharmaceutical tracer that is above a predetermined threshold, and confining detecting said region of the image to only detecting said activity that is above said predetermined threshold in said candidate regions;
   determining for the detected region a regional value in the image data associated with the pharmaceutical tracer;
   using the regional value to determine an amount of the pharmaceutical tracer in the region;
   subtracting said amount from the specified amount of the pharmaceutical tracer to obtain a corrected amount of the pharmaceutical tracer; and
   making an indication of the corrected amount available from the processor.

2. A method according to claim 1, wherein the variable is said activity produced by the pharmaceutical tracer.

3. A method according to claim 2, comprising determining said region value by measuring an SUV value for the region.

4. A method according to claim 1, further comprising determining an average concentration of said activity in the identified region, and a volume of said region, and determining a total activity in the identified region as a product of said average concentration and said volume.

5. A method according to claim 4, wherein the steps of using and subtracting comprise:
   subtracting the total activity from a decay-corrected dose introduced into the subject.

6. A method according to claim 1, wherein the identified region is an infiltration site of the subject.

7. A method according to claim 1, comprising detecting the region as comprising one or more voxels having a value of SUV over the threshold.

8. A method according to claim 1, further comprising segmenting the detected region from said image data.

9. A method according to claim 8, comprising segmenting the region using an isocontour at a predetermined percentage of a maximum of said activity for the region.

10. An apparatus for correcting image data from a medical imaging scan of a subject, into which subject a specified amount of pharmaceutical tracer has been introduced, the apparatus comprising:
    an anatomical atlas having anatomical data stored therein;
    a processor configured to access said anatomical data in said anatomical atlas and to compare the image data to said anatomical data, and to identify a set of candidate regions of the image data that correspond respectively to regions in the anatomical atlas marked as likely sites of introduction of the pharmaceutical tracer into the subject;
    a processor configured to detect a region of the image data that represents activity produced by said pharmaceutical tracer that is above a predetermined threshold, and to confine detecting said region of the image to only detecting said activity that is above said predetermined threshold in said candidate regions, and to determine for the detected region a regional value in the image data associated with the pharmaceutical tracer, and to use the regional value to determine an amount of the pharmaceutical tracer in the region, and to subtract said amount from the specified amount of the pharmaceutical tracer to obtain a corrected amount of the pharmaceutical tracer; and
    a monitoring device at which the processor is configured to indicate the corrected amount of the pharmaceutical tracer to a user.

11. A non-transitory, computer-readable data storage medium encoded with programming instructions, said data storage medium being loaded into a computerized processor that is supplied with image data from a medical imaging scan of a subject, into which subject a specified amount of pharmaceutical tracer has been introduced, said programming instructions causing said computerized processor to:
    access anatomical data in an anatomical atlas and compare the image data to said anatomical data, and identify a set of candidate regions of the image data that correspond respectively to regions in the anatomical atlas marked as likely sites of introduction of the pharmaceutical tracer into the subject;
    detect a region of the image data that represents activity produced by said pharmaceutical tracer that is above a predetermined threshold and confine detecting said region of the image to only detecting said activity that is above said predetermined threshold in said candidate regions;
    determine for the detected region a regional value in the image data associated with the pharmaceutical tracer;
    use the regional value to determine an amount of the pharmaceutical tracer in the region;
    subtract said amount from the specified amount of the pharmaceutical tracer to obtain a corrected amount of the pharmaceutical tracer; and
    make an indication of the corrected amount available from the processor.

* * * * *